United States Patent
Hutchin

(10) Patent No.: US 7,618,144 B2
(45) Date of Patent: Nov. 17, 2009

(54) SYSTEM AND METHOD FOR TRACKING EYE MOVEMENT

(75) Inventor: Richard A. Hutchin, Calabasas, CA (US)

(73) Assignee: Optical Physics Company, Calahasis, CA (US)

( * ) Notice: Subject to any disclaimer, the term of this patent is extended or adjusted under 35 U.S.C. 154(b) by 0 days.

(21) Appl. No.: 11/970,330

(22) Filed: Jan. 7, 2008

(65) Prior Publication Data

US 2009/0174864 A1    Jul. 9, 2009

(51) Int. Cl.
*A61B 3/14* (2006.01)
*A61B 3/10* (2006.01)

(52) U.S. Cl. ........................... 351/210; 351/211

(58) Field of Classification Search .......... 351/200–246
See application file for complete search history.

(56) References Cited

U.S. PATENT DOCUMENTS 6,592,574 B1 *   7/2003   Shimmick et al. .............. 606/4
6,607,527 B1 *   8/2003   Ruiz et al. .................... 606/41

* cited by examiner

*Primary Examiner*—Mohammed Hasan
(74) *Attorney, Agent, or Firm*—Connolly Bove Lodge & Hutz LLP

(57) ABSTRACT

A system for tracking eye movement is disclosed. A first light source, emitting light including a first wavelength, is adapted to illuminate corneal tissue of an eye. The first wavelength is selected such that it is strongly absorbed by corneal tissue. A position sensitive detector is adapted to detect a reflection of light at the first wavelength off the corneal tissue. Signal may be generated in response to the detected reflection which are representative of the position of the reflection, and therefore the position of the corneal tissue, with respect to the position sensitive detector.

31 Claims, 3 Drawing Sheets

SYSTEM AND METHOD FOR TRACKING EYE MOVEMENT

BACKGROUND OF THE INVENTION

1. Field of the Invention

The field of the present invention is systems and methods for tracking eye movement.

2. Background

Four different types of non-contact eye trackers are generally known in the prior art. Of the four, the limbus eye tracker is the simplest and least expensive. The limbus eye tracker aims two pulsed infrared photo-emitters at the iris-sclera boundary on either side of the eye. Because of the difference in color between the iris and sclera, differing amounts of light are reflected depending on the position of the eye relative to the emitter. A pair of infrared detectors picks up the reflected light from the emitters, and the differential signal from the emitters is demodulated and filtered to provide a signal proportional to horizontal eye position. This technique provides a relatively easy-to-use recording method, but it does have substantial drawbacks. First, it is limited to tracking horizontal eye movement, and cannot track vertical eye movement. In addition, the two photo emitters and the pair of infrared detectors must be held immobile with respect to the user's head. Any relative movement between the head and the photo emitters or the infrared detectors can create substantial errors in the tracking data.

Another technique, which is very similar to limbus tracking, tracks the boundary between the pupil and the iris. As with limbus tracking, the emitters and detectors of the apparatus must be immobilized in relation to the head. However, this technique does offer the advantage of being able to track vertical movement of the eye because the pupil is far less covered by the eyelids than the limbus. Another advantage is that the border of the pupil is often sharper than that of the limbus, thus yielding a higher resolution. The advantage of using the pupil boundary for tracking purposes, however, also carries an inherent disadvantage in that the difference in contrast is lower between the pupil and iris than between the iris and sclera, thus making detection of the boundary more difficult.

In another technique, the relative positions between reflections from the cornea and lens are used to track eye movement. When light is shone into an eye, several reflections occur at the boundaries of the lens and cornea. These are the so-called Purkinje images, the first of which is also called the "glint". An image of light, typically referred to as the "bright-eye", is simultaneously reflected off the retina. Images of the bright-eye and glint can be recorded, using an infrared sensitive camera, as a very bright spot and a less bright disc, respectively. When the eye is panned horizontally or vertically, the relative positioning of the glint and the center of the bright-eye change with the movement. From the relative positions of the glint and the bright-eye, the direction of gaze can be determined.

A fourth eye tracking technique also uses Purkinje images. Such eye trackers measure the relative displacement of the images formed by the reflection of a light source at the anterior corneal surface and the posterior lens surface, which are known as the $1^{st}$ and $4^{th}$ Purkinje images, respectively. Rotation of the eye results in a greater displacement of the $1^{st}$ Purkinje image relative to the $4^{th}$ Purkinje image, thereby providing a signal proportional to eye position. The primary drawback of such eye trackers is that they require precise alignment and are not suitable under circumstances where the subject is permitted to have relatively free head movement.

SUMMARY OF THE INVENTION

The present invention is directed toward a system and a method for tracking eye movement. The system includes a light source and a position sensitive detector. The light source emits light which includes a first wavelength, wherein light at the first wavelength is strongly absorbed by corneal tissue, and is adapted to illuminate corneal tissue of the eye. The position sensitive detector is adapted to detect a reflection of light at the first wavelength off the corneal tissue. With such a system, the rotational position of the cornea, with respect to the position sensitive detector, may be determined by using the signal output from the position sensitive detector.

The system may be enhanced by including a second light source emitting light which includes a second wavelength, wherein light at the second wavelength is strongly absorbed by scleral tissue. The second light source is adapted to illuminate scleral tissue of the eye, and the position sensitive detector is adapted to detect a second reflection of light off the scleral tissue. With this enhancement, the position of the eye, with respect to the position sensitive detector, may be determined. Optionally, the first and second wavelengths may be the same wavelength, with the corneal tissue and the scleral tissue being alternately illuminated. This may be accomplished through the use of multiple light sources, with the phase of the pulses differing by 180°.

The method for tracking eye movement involves first illuminating corneal tissue with light including a first wavelength, this first wavelength being one that is strongly absorbed by the corneal tissue. A reflection of light at the first wavelength off the corneal tissue is then detected, and a signal representative of the position of the first reflection is then generated. With this signal, the rotational position of the cornea may be determined. Similar to the system, the method may be enhanced by also illuminating scleral tissue with light including a second wavelength, wherein light at the second wavelength is strongly absorbed by scleral tissue. A second reflection of light, this one being at the second wavelength and off the scleral tissue, is then detected. As with the first reflection, a signal representative of the position of the second reflection may be generated. Optionally, the corneal tissue and the scleral tissue may be alternately illuminated, thereby facilitating use of the same wavelength for the first wavelength and the second wavelength.

Accordingly, an improved system and an improved method of tracking eye movement are disclosed. Advantages of the improvements will appear from the drawings and the description of the preferred embodiment.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
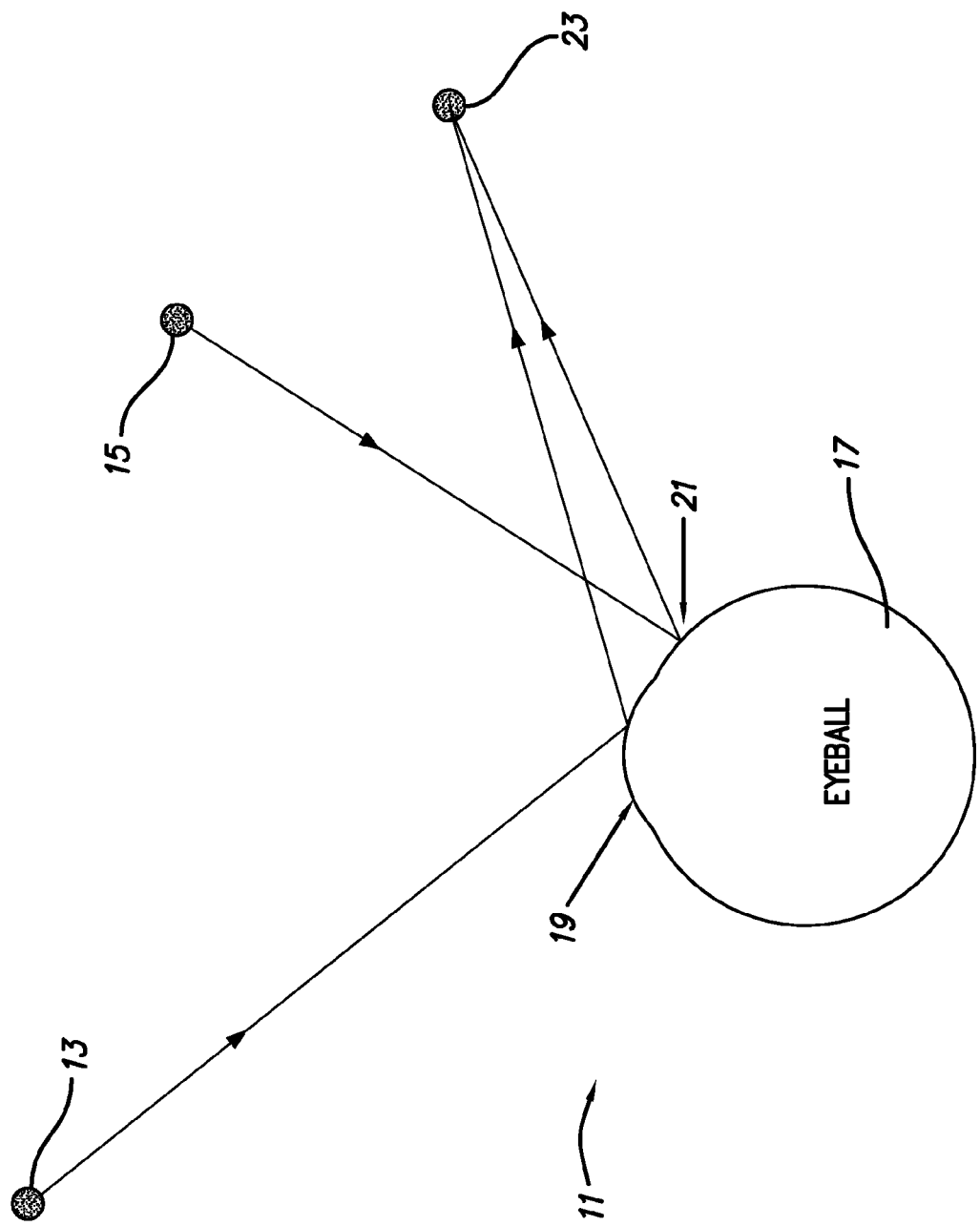
FIG. 1 schematically illustrates a system for tracking eye movement from a top elevation view of the eye.

Turning in detail to the drawings, FIG. 1 illustrates a basic system 11 for tracking eye movement. Two light sources 13, 15 are positioned to direct light toward the eye 17, with the first light source 13 directing light toward the cornea 19, and the second light source 15 directing light toward the sclera 21. Both light sources emit light at a wavelength which is strongly absorbed by the tissues of the eye. While the system 11 may be constructed with the two light sources 13, 15 having different wavelengths, in the illustrated system 11 both construction and operation are simplified by pulsing the two light sources 13, 15 with a phase difference of 180° and operating them at the same wavelength. Alternatively, a single light source could be used in combination with appropriate light guides and optical switches.

By selecting a wavelength that is strongly absorbed by tissues of the eye, no significant reflections are seen from internal structures of the eye. In particular, reflections from the iris and retina are preferably minimized to the extent that the intensities of reflections from these internal structures are less than 1% of the intensity of reflections from outer surfaces of the eye. While many different wavelengths may be used, wavelengths in the range of 1300 nm to 1600 nm, and in particular a wavelength of 1450 nm, are appropriate choices when emitted from low-power sources, as these wavelengths are recognized as being non-harmful to tissues at low powers, even with constant exposure over a period of several hours. Other wavelengths outside this range, if found to be strongly absorbed and eye-safe, might also be used. By eliminating reflections from internal structures, such as the iris and the retina, the eyeball appears as a black featureless orb with a bulge representing the cornea. Without interference from reflections off internal surfaces, the reflections from both the cornea and the sclera easily tracked by a single position sensitive detector (PSD) 23, although multiple PSDs could also be used.

The PSD 23 is positioned to receive both the reflection off the cornea 19 from the first light source 13 and the reflection off the sclera 21 from the second light source 15. The spatial relationship between the PSD 23 with respect to each of the two light sources 13, 15, is fixed. As the gaze of the eye moves, the reflection off the cornea 19, and its position on the PSD 23, likewise moves. By knowing the position of the first light source 13 and the PSD 23 with respect to the eye 17, the position of the reflection off the cornea 19 on the PSD 23 enables the direction of gaze to be determined. Depending upon the type of PSD used, it is estimated that the direction of gaze with respect to the PSD 23 can be determined to better than 1 milliradian accuracy. While a system in which the first light source 13 and the PSD 23 are in fixed positions with respect to the eye are easily achieved in a laboratory, inclusion of the second light source 15 facilitates real world applications for the eye tracker. The position of the reflection off the sclera 21 enables the position of the PSD 23 with respect to the eye 17 to be determined. As the relative position between the eye 17 and the PSD 23 moves, the position of the reflection off the sclera 21 moves on the PSD 23. This enables tracking of the spatial relationship between the eye 17 and the PSD 23. This tracking information is utilized to correct for movement of the PSD with respect to the eye, so that the direction of gaze may be determined with consistent accuracy.

While the system described above is capable of tracking movement, and thus the gaze, of a single eye, two such systems may be used in combination to track movement of both an individual's eyes, thereby allowing more accurate tracking of the direction of the individual's gaze over a larger field of regard. For a single eye, the above system is capable of tracking the horizontal position of an eye from about −20° to about +50° and the vertical position from about −30° to +30°. By tracking both eyes the horizontal tracking capabilities extend from about −50° to about +50°. In addition, tracking both eyes allows a measurement of the vergence between the gaze of each eye, and the vergence can be used to estimate the range of the object being viewed.

Figure 2:
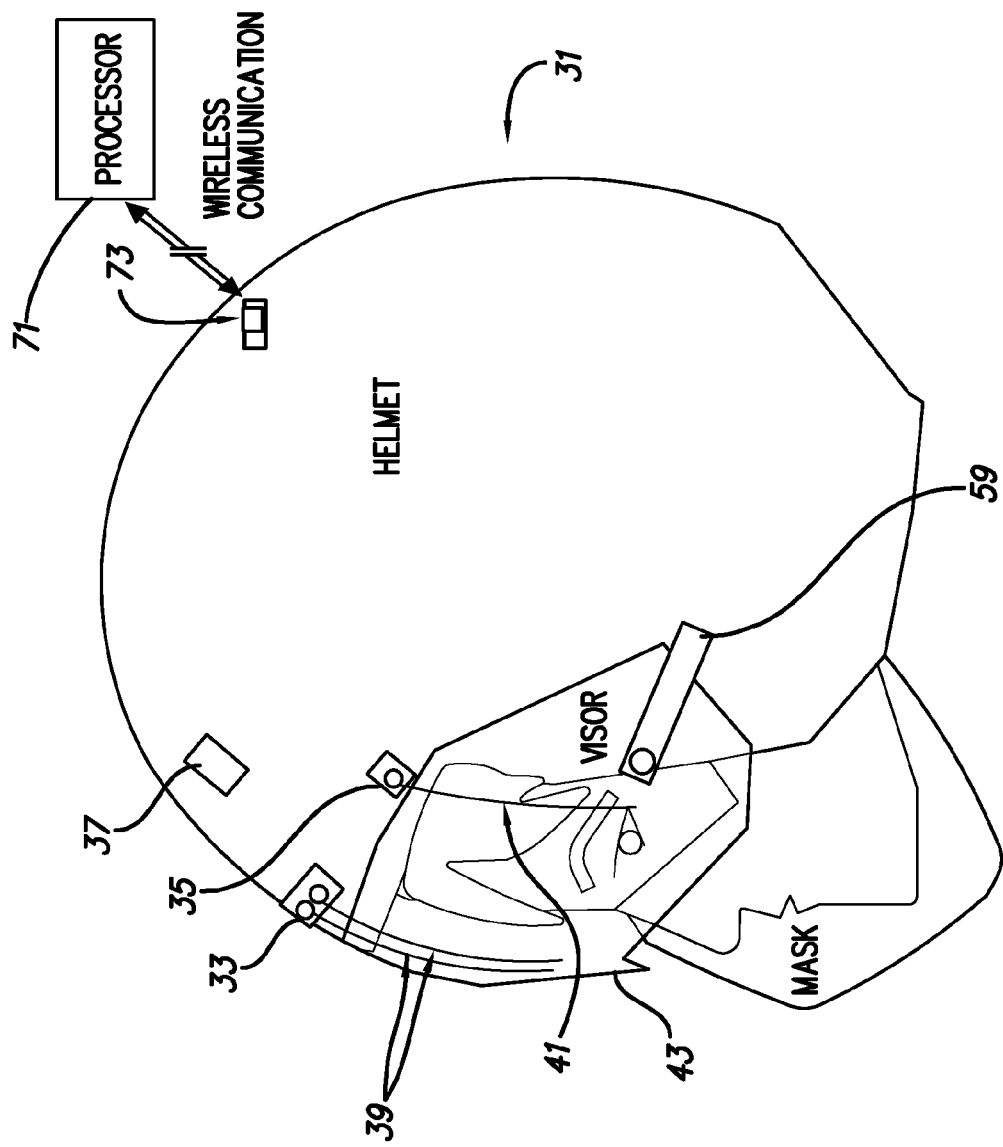
FIG. 2 illustrates a system for tracking eye movement incorporated into a helmet.
Figure 3:
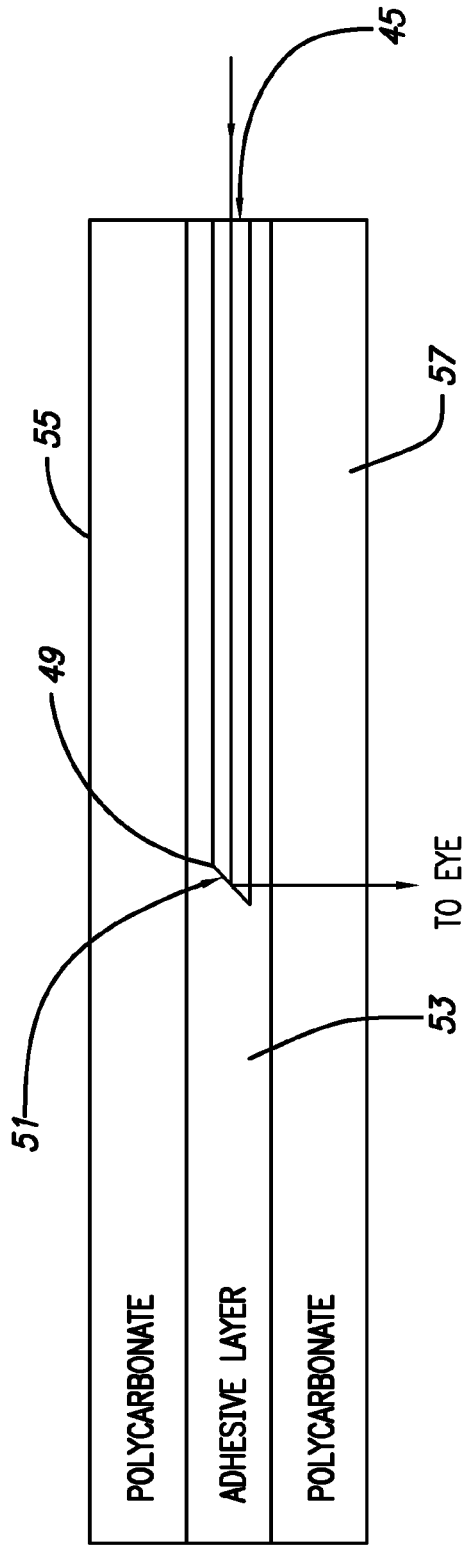
FIG. 3 illustrates a fiber bonded between two layers of a visor.

FIG. 2 shows a flight helmet 31 with tracking systems for both of the wearer's eyes. Two Infrared diodes 33 are mounted to the helmet 31 to serve as light sources for illuminating the cornea. Two more infrared diodes 35 (only one is shown in this profile view) are similarly mounted to the helmet 31 to serve as light sources for illuminating the sclera of each eye. Each of the infrared diodes 33, 35 is electronically linked to a controller 37, also mounted to the helmet 31, which controls the rate and timing of light pulses from each diode. For this purpose, a simple oscillating circuit suffices for the controller 37. Fibers 39, 41 are embedded into, or applied to a surface of, the visor 43, with each fiber 39, 41 receiving light from one of the laser diodes 33, 35. The two fibers 39 used for illuminating cornea tissue of each eye are shown mounted in the visor 43 over the nose bridge, although other positions could also be used. The other two fibers 41, used for illuminating sclera tissue, extend down to the outer corners of each eye, although here, too, other positions could be used. The end 49 of each fiber is cut at an angle, as is shown in FIG. 3, and a reflective coating is applied to the cut surface 51. The end of the fiber and the reflective coating 51 are positioned within the visor 43 to direct light toward each respective eye.

FIG. 3 also shows one method of embedding the fibers in the visor 43 that uses refractive index matching to render the embedded fiber virtually invisible to the wearer. A fiber 45 is placed in an adhesive layer 53 between two layers of polycarbonate 55, 57, with the adhesive layer 53 having an index of refraction that is closely matched to the index of refraction of the fiber cladding.

Figure 4:
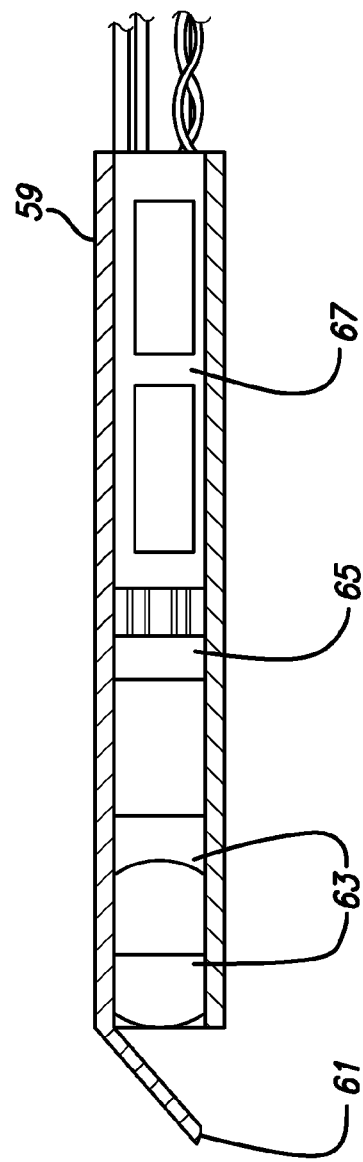
FIG. 4 illustrates a sensor module.

Referring to FIGS. 2 & 4, two sensor tubes 59 are mounted to the helmet 31, one on each side of the visor 43, and positioned to receive light emitted from the fibers 39, 41 as reflected off both the cornea and sclera, respectively. By placing the sensor tubes 59 on the side of the user's face, the system is still capable of tracking gaze even when the eyelids droop or lower to partially cover the eyes. Both sensor tubes 59 are constructed with the same design.

The sensor tube 59 includes a mirror 61 positioned to direct light into the sensor tube 59 and cylindrical imaging lenses 63 which focus an image of the reflected light onto the PSD 65. The PSD 65 measures the position of the image in the x and y directions on the sensor plane and generates output signals corresponding to the position. The (x,y) position of the focused spot on the PSD 65 correlates to the direction of light reflected by the eye, and this position moves as the direction of gaze shifts. The circuitry 67 within the sensor tube 59 measures and digitizes the signals from the PSD 65 and is electronically coupled to the controller 37 so that the reflections can be sampled synchronously with the respective diode pulses. In a flight helmet, the PSD 65 and associated circuitry 67 preferably sample the spot position at about 200 Hz. Other applications may use greater or lesser sampling rates. The digitized signals from the circuitry 67 are sent to a processor 71 via a wireless infrared communication link 73. Using the known geometry of the tracking system and calibration data, the processor is enabled to track the gaze of the individual wearing the helmet 31. Calibration data is obtained and used to provide full eye tracking accuracy since eyes vary in size, spacing, and position amongst different individuals.

The processor 71 may be a personal computer, the computerized systems on board an aircraft, or any other type of programmable processor, and the infrared communication link 73 is of a type commonly known in the prior art. Depending upon the environment in which the eye tracker is used, the communication link may use other forms of wireless technology, or alternatively, a wired link may be used.

Thus, a system and a method of tracking eye movement are disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A system for tracking eye movement, the system comprising:
   a first light source emitting light including a first wavelength, wherein the first light source is adapted to illuminate corneal tissue of an eye, light at the first wavelength being strongly absorbed by corneal tissue;
   a position sensitive detector adapted to detect a first reflection of light at the first wavelength off the corneal tissue; and
   a second light source emitting light including a second wavelength, wherein the second light source is adapted to illuminate scleral tissue of the eye, light at the second wavelength being strongly absorbed by scleral tissue.

2. The system of claim 1, wherein the position sensitive detector is adapted to generate a signal corresponding to a position of the first reflection.

3. The system of claim 1, wherein the position sensitive detector is adapted to detect a second reflection of light at the second wavelength off the scleral tissue.

4. The system of claim 3, wherein the position sensitive detector is adapted to generate a signal corresponding to a position of the second reflection.

5. The system of claim 1, wherein the first and second light sources each comprise a pulsed light source, with the first and second light sources differing in phase by 180°.

6. The system of claim 5, wherein the first wavelength is the second wavelength.

7. The system of claim 1, wherein the first wavelength is in the range of 1300 nm to 1600 nm.

8. The system of claim 7, wherein the first wavelength is 1450 nm.

9. A system for tracking movement of both eyes of an individual, the system comprising:
   at least one light source emitting light including a first wavelength, wherein light from the light source is adapted to illuminate corneal tissue of each eye, light at the first wavelength being strongly absorbed by corneal tissue;
   a first position sensitive detector adapted to detect a first reflection of light at the first wavelength off the corneal tissue of the first eye;
   a second position sensitive detector adapted to detect a second reflection of light at the first wavelength off the corneal tissue of the second eye; and
   at least one second light source emitting light including a second wavelength, wherein light from the second light source is directed toward scleral tissue of each eye, light at the second wavelength being strongly absorbed by scleral tissue.

10. The system of claim 9 wherein the first position sensitive detector is adapted to generate a signal corresponding to a position of the first reflection.

11. The system of claim 9 wherein the second position sensitive detector is adapted to generate a signal corresponding to a position of the second reflection.

12. The system of claim 9, wherein the first position sensitive detector is adapted to detect a third reflection of light at the second wavelength off the scleral tissue of the first eye.

13. The system of claim 12, wherein the first position sensitive detector is adapted to generate a signal corresponding to a position of the third reflection.

14. The system of claim 9, wherein the second position sensitive detector is adapted to detect a fourth reflection of light at the second wavelength off the scleral tissue of the second eye.

15. The system of claim 14, wherein the second position sensitive detector is adapted to generate a signal corresponding to a position of the fourth reflection.

16. The system of claim 9, wherein the first and second light sources each comprise a pulsed light source, with the first and second light sources differing in phase by 180°.

17. The system of claim 9 wherein the second wavelength is the first wavelength.

18. The system of claim 9, wherein the first wavelength is in the range of 1300 nm to 1600 nm.

19. The system of claim 18, wherein the first wavelength is 1450 nm.

20. A method for tracking eye movement, the method comprising:
   illuminating corneal tissue with light including a first wavelength, wherein light at the first wavelength is strongly absorbed by corneal tissue;
   detecting a first reflection of light at the first wavelength off the corneal tissue;
   generating a signal representative of a position of the first reflection;
   illuminating scleral tissue with light including a second wavelength, wherein light at the second wavelength is strongly absorbed by scleral tissue; and
   detecting a second reflection of light at the second wavelength off the scleral tissue.

21. The method of claim 20, further comprising alternately illuminating the corneal tissue and illuminating the scleral tissue.

22. The method of claim 20, wherein generating the signal includes generating the signal to be further representative of a position of the second reflection.

23. The method of claim 20, wherein the first wavelength is the second wavelength.

24. The system of claim 20, wherein the first wavelength is in the range of 1300 nm to 1600 nm.

25. The method of claim 24, wherein the first wavelength is 1450 nm.

26. A method for tracking movement of both eyes of an individual, the method comprising:
   illuminating corneal tissue of both eyes with light including a first wavelength, wherein light at the first wavelength is strongly absorbed by corneal tissue;
   detecting a first reflection of light at the first wavelength off the corneal tissue of the first eye;
   detecting a second reflection of light at the first wavelength off the corneal tissue of the second eye;
   generating a signal representative of positions of the first and second reflections;
   illuminating scleral tissue of both eyes with light including a second wavelength, wherein light at the second wavelength is strongly absorbed by scleral tissue;
   detecting a third reflection of light at the second wavelength off the scleral tissue of the first eye; and
   detecting a fourth reflection of light at the second wavelength off the scleral tissue of the second eye.

27. The method of claim 26, further comprising alternately illuminating the corneal tissue and illuminating the scleral tissue.

28. The method of claim 26, wherein generating the signal includes generating the signal to be further representative of positions of the third and fourth reflections.

29. The method of claim 26, wherein the first wavelength is the second wavelength.

30. The system of claim 26, wherein the first wavelength is in the range of 1300 nm to 1600 nm.

31. The method of claim 30, wherein the first wavelength is 1450 nm.

* * * * *